(12) United States Patent  
Jung et al.

(10) Patent No.: US 8,796,639 B2  
(45) Date of Patent: Aug. 5, 2014

(54) TARGET FOR GENERATING POSITIVE IONS, METHOD OF FABRICATING THE SAME, AND TREATMENT APPARATUS USING THE TARGET

(71) Applicant: Electronics and Telecommunications Research Institute, Daejeon (KR)

(72) Inventors: Moon Youn Jung, Daejeon (KR); Hyeon-Bong Pyo, Daejeon (KR); Dong-Ho Shin, Daejeon (KR); Seunghwan Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 13/919,960

(22) Filed: Jun. 17, 2013

(65) Prior Publication Data

US 2014/0135562 A1    May 15, 2014

(51) Int. Cl.  
*H01J 27/24* (2006.01)  
*H01J 3/04* (2006.01)  
*H01J 27/02* (2006.01)

(52) U.S. Cl.  
CPC ............... *H01J 27/24* (2013.01); *H01J 27/02* (2013.01); *H01J 27/022* (2013.01); *H01J 3/04* (2013.01)  
USPC ...................... 250/423 P; 250/423 R; 250/424

(58) Field of Classification Search  
CPC ............. H01J 3/04; H01J 3/14; H01J 27/00; H01J 27/02; H01J 27/022; H01J 27/16; H01J 27/24; H01J 27/26  
USPC ................... 250/423 R, 424, 423 P, 423 F; 315/111.01, 111.21, 111.81  
See application file for complete search history.

(56) References Cited

U.S. PATENT DOCUMENTS

2005/0269559 A1*  12/2005  Zhou et al. ................... 257/10  
2006/0065828 A1*  3/2006  Lu et al. ....................... 250/288

OTHER PUBLICATIONS

Palchan et al. "Generation of fast ions by an efficient coupling of high power laser into snow nanotubes", Applied Physics Letters 91, 251501 (2007), pp. 251501-1 through 251501-3.*

* cited by examiner

*Primary Examiner* — Nicole Ippolito

(57) ABSTRACT

Provided is an ion beam treatment apparatus. The treatment apparatus includes a target for generating positive ions including a thin film for generating positive ions and nanowires disposed on at least one side of the thin film for generating positive ions, and a laser for emitting a laser beam incident on nanowires to project positive ions to a tumor region of a patient by generating the positive ions from the thin film for generating positive ions. Each of the nanowires may include a metal nanocore and a polymer shell surrounding the metal nanocore. The laser beam incident on the nanowires forms surface plasmon resonance, a near field having an intensity enhanced more than an intensity of the laser beam is formed by the surface plasmon resonance, and the positive ions are emitted from the thin film for generating positive ions by the near field.

20 Claims, 13 Drawing Sheets

Fig. 11A
Fig. 11B
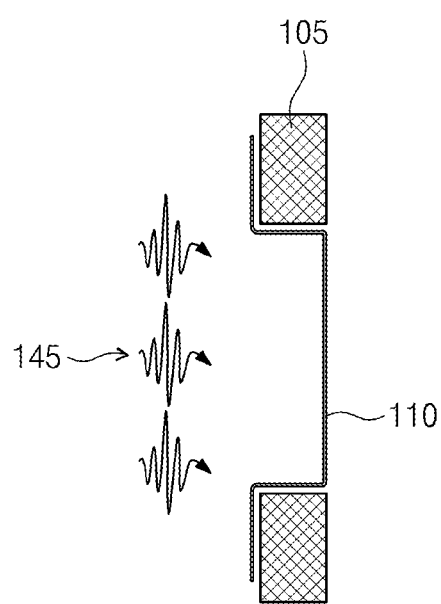
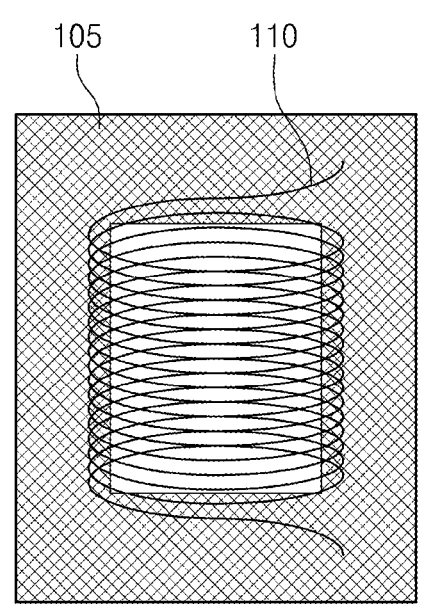

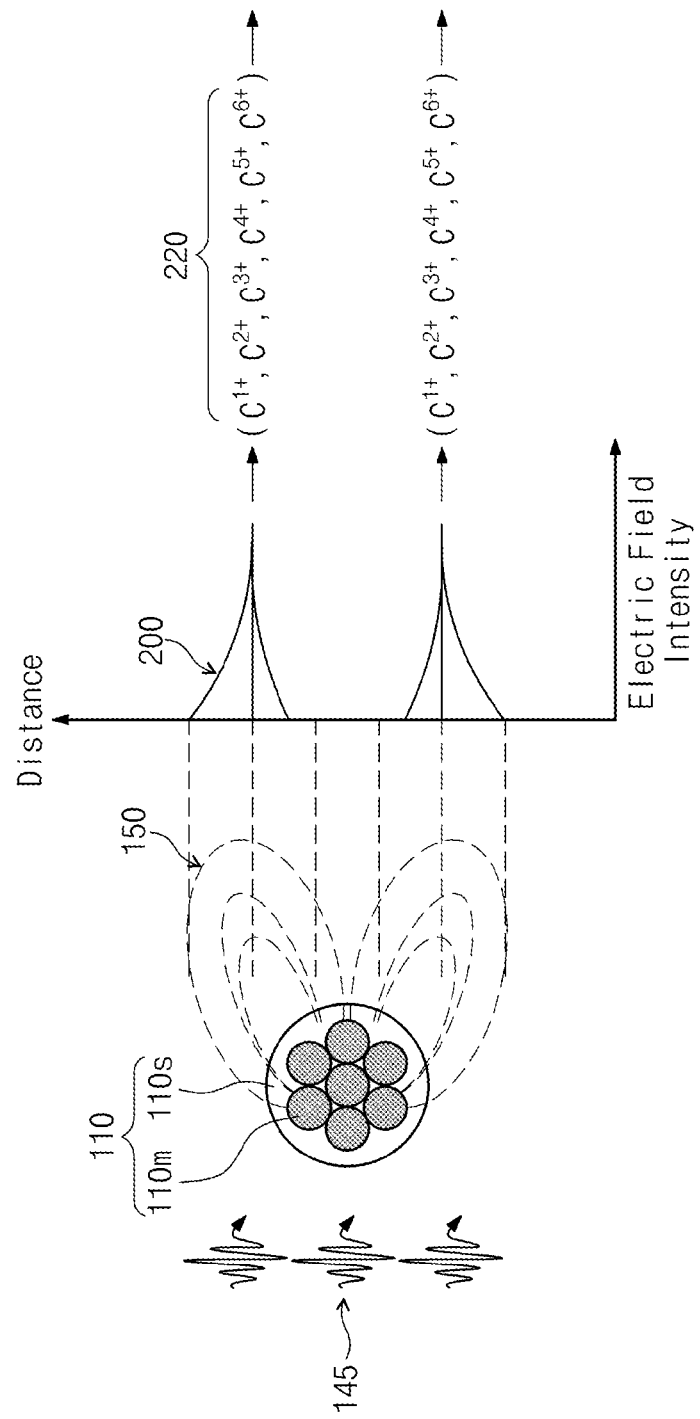

TARGET FOR GENERATING POSITIVE IONS, METHOD OF FABRICATING THE SAME, AND TREATMENT APPARATUS USING THE TARGET

CROSS-REFERENCE TO RELATED APPLICATIONS

This U.S. non-provisional patent application claims priority under 35 U.S.C. §119 of Korean Patent Application No. 10-2012-0128336, filed on Nov. 13, 2012, the entire contents of which are hereby incorporated by reference.

BACKGROUND

The present invention disclosed herein relates to a target for generating positive ions, a method of fabricating the same, and a treatment apparatus using the target, and more particularly, to a target for generating positive ions using surface plasmon resonance, a method of fabricating the same, and an ion beam treatment apparatus using the target.

Radiation treatment methods include X-ray, electron beam, and ion beam treatment methods. Since an X-ray treatment method is the least expensive method that may be realized by using the simplest apparatus, the X-ray treatment method is currently the most commonly used among the radiation treatment methods. That a tumor may be treated when electrons are accelerated by an accelerator to be injected into the tumor is proved in the 1950s. However, an electron beam treatment has been regularly established as a method of radiation treatment after the miniaturization of an electron accelerator was realized in the 1980s. Meanwhile, the X-ray treatment or the electron beam treatment may destruct deoxyribonucleic acid (DNA) of cancer cells by disconnecting hydrogen bonds in the cancer cells, but may be accompanied by a side effect that seriously damages healthy cells located in a progressing path. A technique, such as Intensity-Modulated Radiation Therapy (IMRT) or Tomo Therapy and Cyber Knife, has been developed as a method of reducing radiation exposure with respect to normal cells. However, the above methods may not completely address the foregoing side effect.

An ion beam treatment method has received attention as a treatment measure capable of reducing the side effect generated in the X-ray treatment or the electron beam treatment. In order for an ion beam to transmit a material, the ion beam must have a fast speed by being accelerated as in the case of electrons. Although the speed of an ion beam may be gradually reduced when the ion beam transmits a certain material, the ion beam may experience the highest energy loss of ionizing radiation just before the ion beam stops. Such a phenomenon is referred to as "Bragg Peak", named after William Henry Bragg who discovered the phenomenon in 1903. Therefore, with respect to the ion beam treatment method, a selective as well as localized treatment with respect to malignant tumors may be possible when the speed of ions is accurately controlled. In the case where a tumor is located deep inside the body, protons or ions having relatively high energy must be accelerated from the outside of the body. There is a laser driven ion acceleration method among methods of accelerating such protons or ions. When a thin film is irradiated with a high-power laser beam, ions or protons in the thin film may escape from the thin film while having acceleration energy by a target normal sheath acceleration (TNSA) model or a radiation pressure acceleration (RPA) model. A general principle of the ion beam treatment may be described by that the escaped ions may transmit the body of a patient as deep as the energy of each ion and may stop at a predetermined depth at which a tumor is located, and tumor cells are necrotized while a large amount of free oxygen radicals is generated in the stopped region.

There are broadly two properties that ions must have in the ion beam treatment method using the laser driven ion acceleration method. Ions must be in a state of high energy in order to be injected deep into the body and most of the ions must have the same energy. Protons having an energy of about 250 MeV may transmit about 20 cm of the body. With respect to an ocular cancer treatment, high-energy ions having an energy of about 70 MeV are required and with respect to the treatment of cancer located deep inside the body, high-energy ions having an energy of about 200 MeV or more are required.

Also, energies of most of protons or ions driven by a femtosecond laser must be uniform. The reason for this is that when the energies are not uniform, ions may not be focused only to the position of a tumor, and thus, there may be possibility that normal tissues may be exposed by the ions.

In order to satisfy the above two properties, a thickness of a target as a source of ions must be very small. Therefore, the target must be an ultra thin film.

A laser for accelerating such ions must have a relatively high energy ranging from about $10^{19}$ W/cm$^2$ to about $10^{21}$ W/cm$^2$. This means a relatively large laser system and thus, a large budget may be required.

SUMMARY

The present invention provides a target for generating positive ions that may generate high-energy positive ions.

The present invention also provides a method of fabricating a target for generating positive ions that may generate high-energy positive ions.

The present invention also provides an ion beam treatment apparatus using a target for generating positive ions that may generate high-energy positive ions.

The object of the present invention is not limited to the aforesaid, but other objects not described herein will be clearly understood by those skilled in the art from descriptions below.

Embodiments of the present invention provide targets for generating positive ions. The targets may include a thin film for generating positive ions and nanowires provided on at least one side of the thin film for generating positive ions. Each of the nanowires may include a metal nanocore and a polymer shell surrounding the metal nanocore. The thin film for generating positive ions may generate positive ions by a laser beam incident on the nanowires.

In some embodiments, the metal nanocore may be composed of metal nanoparticles. The metal nanoparticles may include gold, silver, copper, or aluminum.

In other embodiments, the nanowires may be formed by electrospinning a polymer solution including the metal nanoparticles.

In still other embodiments, the metal nanocore may have a linewidth ranging from a few tens to a few hundreds of nanometers.

In even other embodiments, the positive ions may be protons, carbon ions, oxygen ions, or nitrogen ions.

In yet other embodiments, the positive ions are protons and the thin film for generating positive ions may include a material containing hydrogen or sodium. The material containing hydrogen or sodium may be silicon nitride, silicon oxide, sodium nitride, sodium oxide, or metal.

In further embodiments, the positive ions are carbon ions and the thin film for generating positive ions may include graphene.

In still further embodiments, the positive ions are protons, carbon ions, oxygen ions, or nitrogen ions, and the positive ions may be generated from the polymer shell.

In even further embodiments, the targets for generating positive ions may further include a support which is attached to an edge of the thin film for generating positive ions and supports the thin film for generating positive ions.

In other embodiments of the present invention, methods of fabricating a target for generating positive ions are provided. The methods may include forming nanowires respectively including a metal nanocore and a polymer shell surrounding the metal nanocore on one side of a thin film for generating positive ions having both opposing sides by using an electrospinning method. The metal nanocore may form surface plasmon resonance by an incident laser beam, a near field having an intensity enhanced more than an intensity of the laser beam may be formed by the surface plasmon resonance, and positive ions may be emitted from the thin film for generating positive ions by the near field.

In some embodiments, the forming of the nanowires by using an electrospinning method may include preparing a polymer solution containing metal nanoparticles, and applying a voltage between the polymer solution and the thin film for generating positive ions.

In other embodiments, the metal nanoparticles may include gold, silver, copper, or aluminum.

In still other embodiments, the nanowires may be formed to allow the metal nanocore to have a linewidth ranging from a few tens to a few hundreds of nanometers.

In even other embodiments, the thin film for generating positive ions may include a material containing hydrogen or sodium, or graphene.

In still other embodiments of the present invention, ion beam treatment apparatuses are provided. The ion beam treatment apparatuses may include the above-described target for generating positive ions, and a laser for emitting a laser beam incident on nanowires to project positive ions to a tumor region of a patient by generating the positive ions from a thin film for generating positive ions. The laser beam incident on the nanowires may form surface plasmon resonance, a near field having an intensity enhanced more than an intensity of the laser beam may be formed by the surface plasmon resonance, and the positive ions may be emitted from the thin film for generating positive ions by the near field.

In some embodiments, the laser may be disposed on a side opposite to a side of the nanowires facing the thin film for generating positive ions.

In other embodiments, the laser beam may be a femtosecond laser beam.

In still other embodiments, a ratio of an intensity of the near field to the intensity of the laser beam ranges from a few tens to a few tens of thousands.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings:

FIGS. 11A and 11B are respectively cross-sectional view and plan view illustrating another target for generating positive ions used in the ion beam treatment apparatus according to the embodiment of the present invention; and FIG. 12 is a configuration view illustrating generation of positive ions from the target for generating positive ions of FIGS. 11A and 11B used in the ion beam treatment apparatus according to the embodiment of the present invention.

DETAILED DESCRIPTION OF THE EMBODIMENTS

Figure 1:
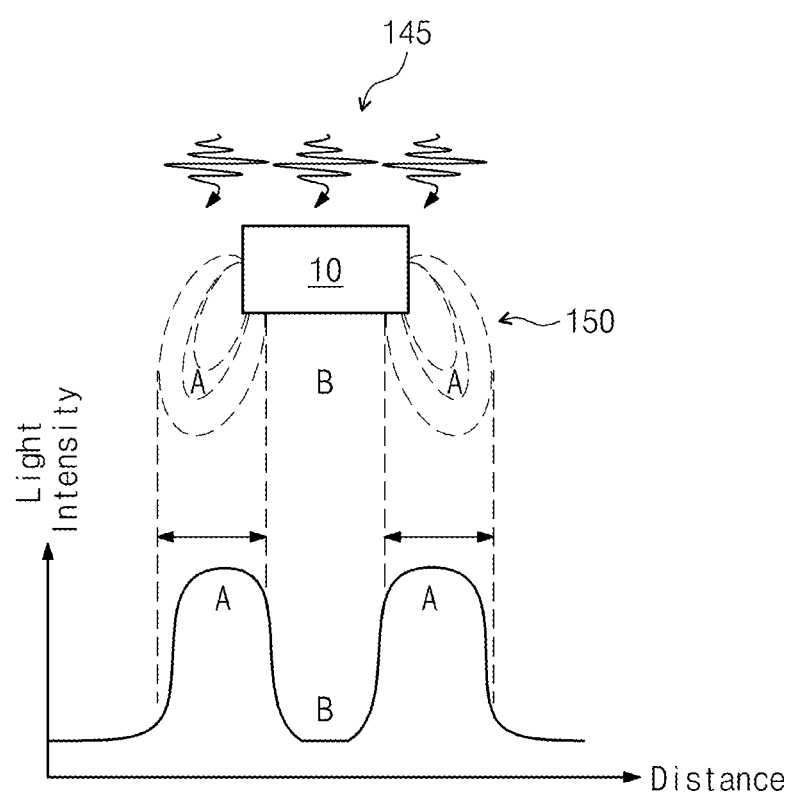
FIG. 1 is a conceptual view illustrating surface plasmon resonance generated in a metal nanomaterial.

Preferred embodiments of the present invention will be described below in more detail with reference to the accompanying drawings. Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. In the drawings, like reference numerals refer to like elements throughout.

In the following description, the technical terms are used only for explaining a specific exemplary embodiment while not limiting the present invention. The terms of a singular form may include plural forms unless referred to the contrary. The meaning of "comprises" and/or "comprising" specifies a property, a region, a fixed number, a step, a process, an element and/or a component but does not exclude other properties, regions, fixed numbers, steps, processes, elements and/or components. Since preferred embodiments are provided below, the order of the reference numerals given in the description is not limited thereto. In addition, it will be understood that when an element such as a layer, film, region, or substrate is referred to as being "on" another element, it can be directly on the other element or intervening elements may also be present.

Additionally, the embodiment in the detailed description will be described with sectional views as ideal exemplary views of the present invention. In the figures, the dimensions of layers and regions are exaggerated for clarity of illustration. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes. For example, an etched region illustrated as a rectangle may have rounded or curved features. Areas exemplified in the drawings have general properties, and are used to illustrate a specific shape of a device region. Thus, this should not be construed as limited to the scope of the present invention.

FIG. 1 is a conceptual view illustrating surface plasmon resonance generated in a metal nanomaterial.

Referring to FIG. 1, when a laser beam 145 is incident on a metal nanomaterial 10, a nanoplasmonic phenomenon occurs at an edge of the metal nanomaterial 10. The nanoplasmonic phenomenon is a result of interaction with free electrons in the metal nanomaterial 10 having nanometer linewidth, wherein surface plasmon resonance, in which light is trapped on a surface of the metal nanomaterial 10, occurs. As the result of the surface plasmon resonance, an intensity of an electromagnetic field is amplified on the surface of the metal nanomaterial 10. That is, a strong near field 150, which is a relatively high electromagnetic field having an intensity amplified about 10 to $10^4$ or more times, occurs in region A near the edge of the metal nanomaterial 10. The near field 150 implies that an intensity of the laser beam 145 incident on the metal nanomaterial 10 is further enhanced. That is, a ratio of the intensity of the near field 150 to the intensity of the laser beam 145 may range from a few tens to a few tens of thousands.

The intensity of the near field 150 is the highest on surfaces of the edge of the metal nanomaterial 10 and decreases as it moves away from the surfaces. The intensity of the near field 150 in region A is relatively higher than that in region B. Region A is a region that is near the edge of the metal nanomaterial 10, and region B is a region that is away from the edge of the metal nanomaterial 10. That is, region B corresponds to a center portion of the nanomaterial 10 or an outer region of the metal nanomaterial 10. Since the center portion of the metal nanomaterial 10 may be less affected by the laser beam 145 that is incident from the outside, the intensity of the near field 150 decreases. However, since the center portion of the metal nanomaterial 10 may be also greatly affected by the laser beam 145 when a size of the metal nanomaterial 10 becomes relatively small, the intensity of the near field 150 may be enhanced.

Figure 2:
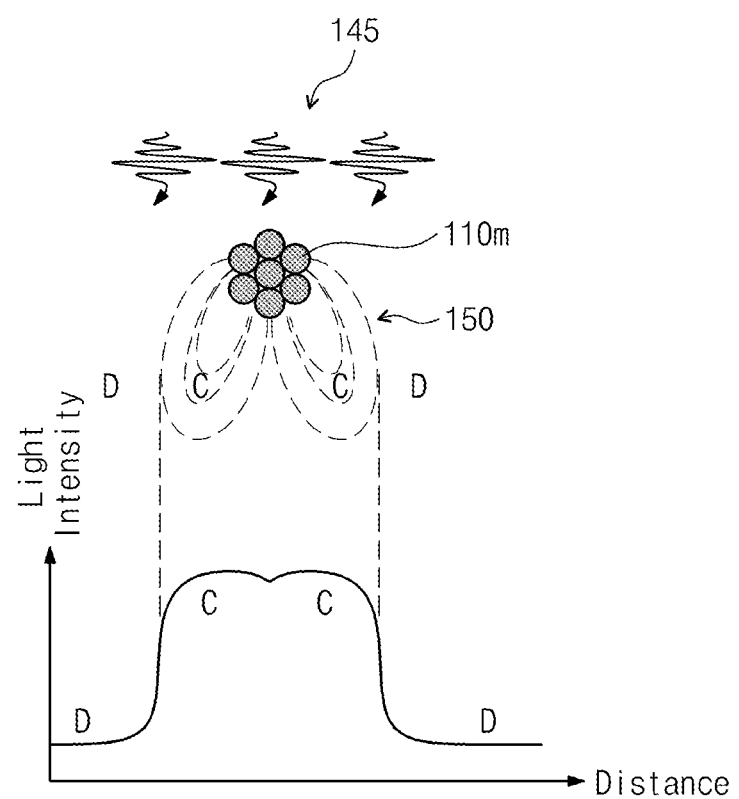
FIG. 2 is a conceptual view illustrating surface plasmon resonance generated in a metal nanocore including metal nanoparticles.

FIG. 2 is a conceptual view illustrating surface plasmon resonance generated in a metal nanocore including metal nanoparticles.

Referring to FIG. 2, when a laser beam 145 is incident on a metal nanocore 110m composed of metal nanoparticles, a strong near field 150, a relatively high electromagnetic field, occurs in entire region C of the metal nanocore 110m including a center portion and a near edge of the metal nanocore 110m. The reason for this is that metal nanoparticles constituting the metal nanocore 110m have a very small size. That is, when the laser beam 145 is incident on the metal nanocore 110m, an intensity of the near field 150 is relatively large in entire region C of the metal nanocore 110m, but the intensity of the near field 150 decreases in outer region D that is away from the metal nanocore 110m.

Figure 3:
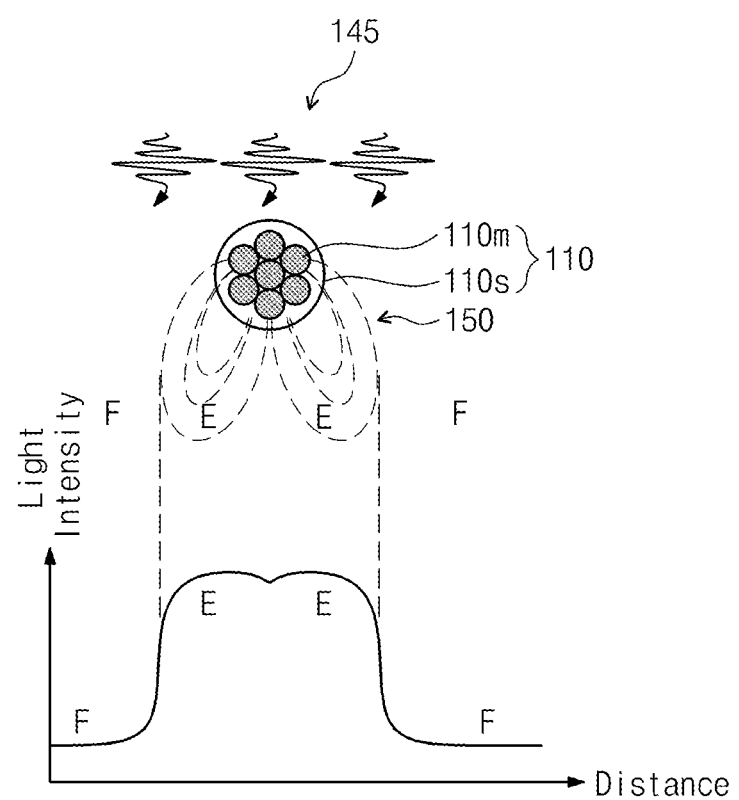
FIG. 3 is a conceptual view illustrating surface plasmon resonance generated in a nanowire of a target for generating positive ions used in an ion beam treatment apparatus according to an embodiment of the present invention.

FIG. 3 is a conceptual view illustrating surface plasmon resonance generated in a nanowire of a target for generating positive ions used in an ion beam treatment apparatus according to an embodiment of the present invention.

Referring to FIG. 3, when a laser beam 145 is incident on a nanowire 110 including a metal nanocore 110m and a polymer shell 110s surrounding the metal nanocore 110m, a strong near field 150, a relatively high electromagnetic field, occurs in entire region E of the metal nanocore 110m including a center portion and a near edge of the metal nanocore 110m of the metal nanowire 110, similar to those described in FIG. 2. The reason for this is that metal nanoparticles constituting metal nanocore 110m have a very small size and the polymer shell 110s is not affected by the laser beam 145. That is, when the laser beam 145 is incident on the nanowire 110, an intensity of the near field 150 is relatively high in entire region E of the metal nanocore 110m of the nanowire 110, but the intensity of the near field 150 decreases in outer region F that is away from the metal nanocore 110m of the nanowire 110.

Figure 4A:
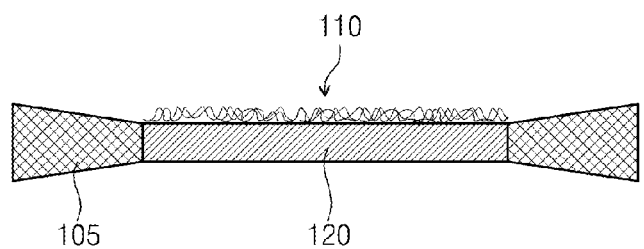
FIG. 4A is a cross-sectional view illustrating a target for generating positive ions used in the ion beam treatment apparatus according to the embodiment of the present invention.
Figure 4B:
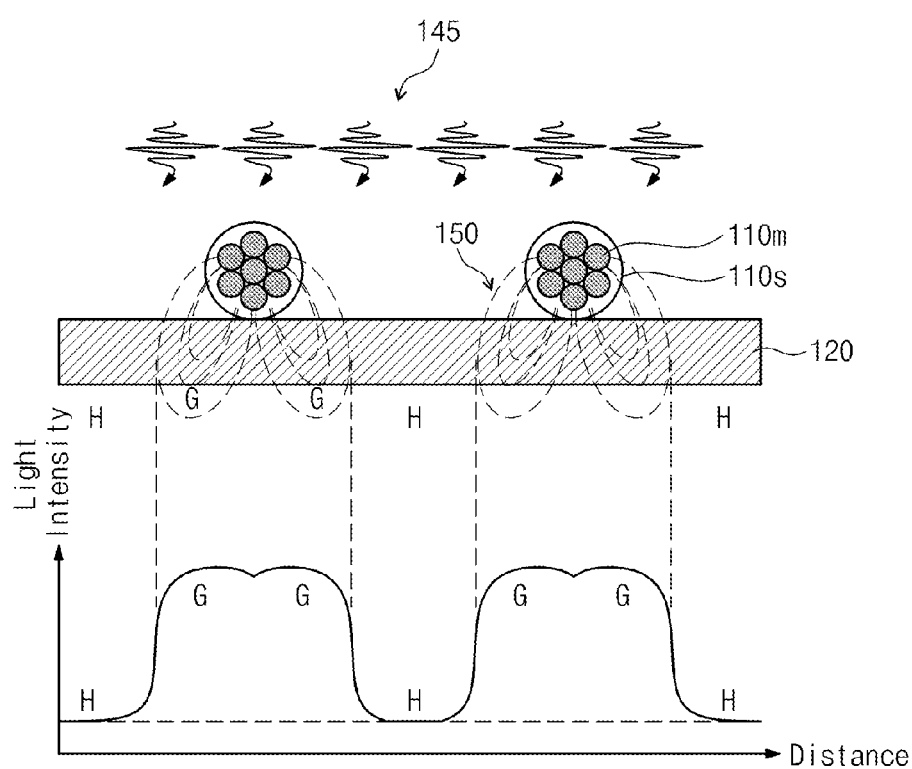
FIG. 4B is a conceptual view illustrating surface plasmon resonance generated in the target for generating positive ions used in the ion beam treatment apparatus according to the embodiment of the present invention.

FIG. 4A is a cross-sectional view illustrating a target for generating positive ions used in the ion beam treatment apparatus according to the embodiment of the present invention, and FIG. 4B is a conceptual view illustrating surface plasmon resonance generated in the target for generating positive ions used in the ion beam treatment apparatus according to the embodiment of the present invention.

Referring to FIGS. 4A and 4B, the target for generating positive ions includes a thin film for generating positive ions 120, nanowires 110 provided on one side of the thin film for generating positive ions 120, and a support 105 capable of fixing and supporting the thin film for generating positive ions 120.

As illustrated in the cross-sectional view of FIG. 4A, the target for generating positive ions may have a configuration in which an edge of the thin film for generating positive ions 120 are attached to the support 105. However, the present invention is not limited thereto. Alternatively, the support 105 may have the shape of a frame, in which the edge of the thin film for generating positive ions 120 are attached to one surface of the support 105 and a center portion of the thin film for generating positive ions 120 is exposed to the outside. That is, the support 105 may support the thin film for generating positive ions 120 and simultaneously, may limit a region irradiated with the laser beam 145.

Each of the nanowires 110 may include a metal nanocore 110m composed of metal nanoparticles and a polymer shell 110s surrounding the metal nanocore 110m. The metal nanocore 110m may have a linewidth of a few tens to a few hundreds of nanometers. The metal nanoparticles may include a material having relatively high electric conductivity, such as gold (Au), silver (Ag), copper (Cu), or aluminum (Al).

The thin film for generating positive ions 120 may generate positive ions (see 210 in FIG. 7) by the incident laser beam

145. The positive ions may be protons, carbon (C) ions, oxygen (O) ions, or nitrogen (N) ions.

In a case where the positive ions are protons, the thin film for generating positive ions 120 may include a material containing hydrogen (H) or sodium (Na). The material containing hydrogen or sodium may be silicon nitride, silicon oxide, sodium nitride, sodium oxide, or metal. Also, in a case where the positive ions are carbon ions, the thin film for generating positive ions 120 may include graphene.

Alternatively, in a case where the positive ions are protons, carbon ions, oxygen ions, or nitrogen ions, the positive ions may not be generated from the thin film for generating positive ions 120, but may be generated from the polymer shell 110s of each of the nanowires 110.

When the laser beam 145 is incident on the nanowires 110, strong near fields 150, relatively high electromagnetic fields, occur in entire regions G of the metal nanocore 110m including a center portion and a near edge of the metal nanocore 110m of each nanowire 110, similar to those described in FIG. 2 or FIG. 3. The reason for this is that metal nanoparticles constituting metal nanocore 110m have a very small size and the polymer shell 110s is not affected by the laser beam 145. That is, when the laser beam 145 is incident on the nanowire 110, an intensity of the near field 150 is relatively high in entire region G of the metal nanocore 110m of each nanowire 110, but the intensity of the near field 150 decreases in region H between the nanowires 110 and outer region H that is away from the metal nanocore 110m of each nanowire 110.

Therefore, strong near fields 150 are induced in regions of the thin film for generating positive ions 120 around the nanowires 110, but only the intensity of the laser beam 145 is transferred to areas of the thin film for generating positive ions 120 in region H between the nanowires 110 having a low intensity of the near field 150. As a result, high-energy positive ions are generated from the regions of the thin film for generating positive ions 120 in which the strong near fields 150 are induced. However, low-energy positive ions, which may not be used in an ion beam treatment apparatus, are generated from the thin film for generating positive ions 120 between the nanowires 110 having a low intensity of the near filed 150.

Figure 5A:
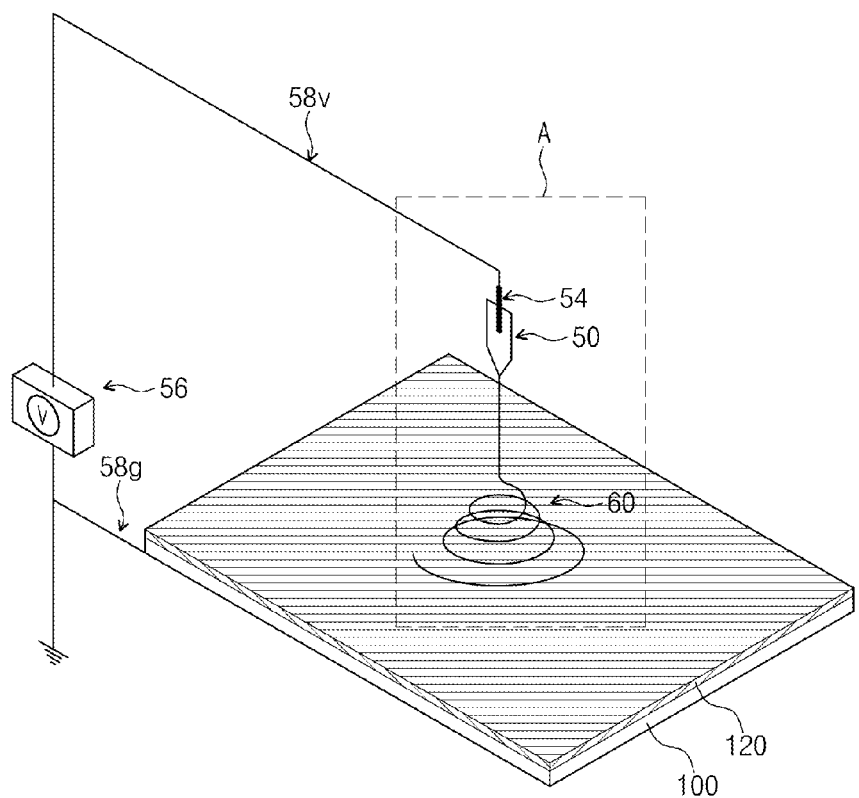
FIG. 5A is a three-dimensional configuration view schematically illustrating a method of fabricating a target for generating positive ions used in the ion beam treatment apparatus according to the embodiment of the present invention.
Figure 5B:
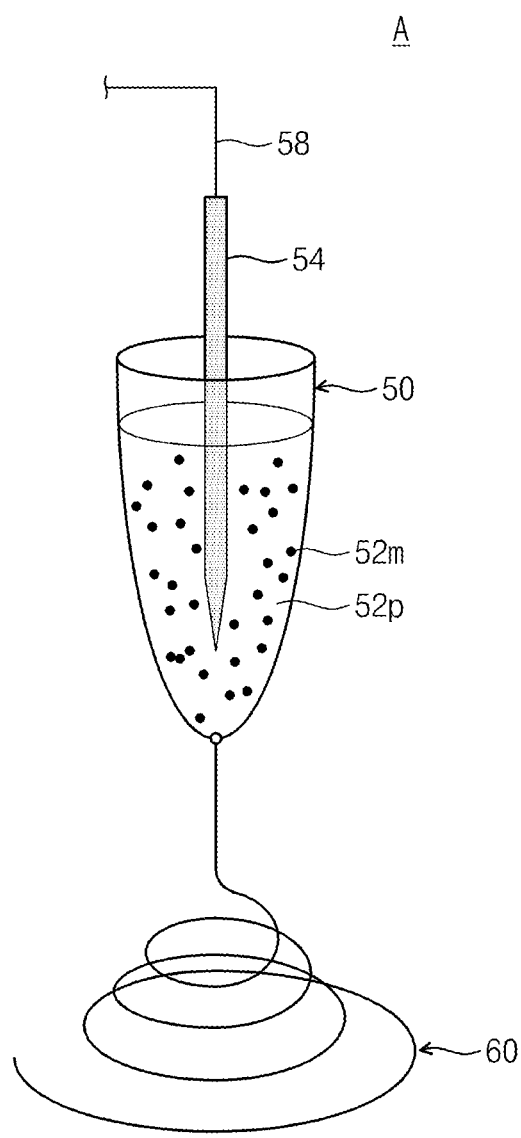
FIG. 5B is a magnified, three-dimensional view of a portion of FIG. 5A.

FIG. 5A is a three-dimensional configuration view schematically illustrating a method of fabricating a target for generating positive ions used in the ion beam treatment apparatus according to the embodiment of the present invention, and FIG. 5B is a magnified, three-dimensional view of a portion of FIG. 5A.

Referring to FIGS. 5A and 5B, nanowires 60 are formed on one side of a thin film for generating positive ions 120 by using an electrospinning method.

An electrospinning apparatus using the electrospinning method may be composed of a grounding substrate 100 having the thin film for generating positive ions 120 disposed thereon, an electrospinning container 50 containing a polymer solution 52p including metal nanoparticles 52m, an electrode 54 for applying a voltage to the polymer solution 52p, a voltage applying device 56, a grounding cable 58g connecting the grounding substrate 100 and the voltage applying device 56, and an application cable 58v connecting the electrode 54 and the voltage applying device 56.

When a voltage ranging from about 500 V to about 3,000 V is applied between the electrode 54 and the grounding substrate 100 having the thin film for generating positive ions 120 disposed thereon, the polymer solution 52p is charged and thus, the nanowires 60 having the shape of a very thin thread with a diameter ranging from about a few tens to about a few hundreds of micrometers may be electrospinned on the thin film for generating positive ions 120 through a spinning hole of the electro spinning container 50. At this time, since the metal nanoparticles 52m contained in the polymer solution 52p are also electrospinned while being included in the electrospinned nanowires 60, the metal nanoparticles 52m may have the form of constituting a metal nanocore (see 110m in FIG. 4) in each of the electrospinned nanowires 60.

Figure 6A:
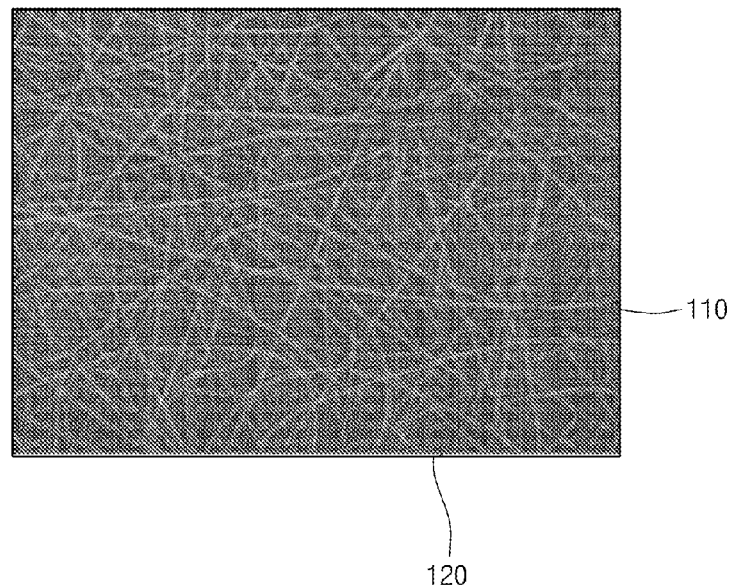
FIG. 6A is a plan-view image of a target for generating positive ions used in the ion beam treatment apparatus according to the embodiment of the present invention.
Figure 6B:
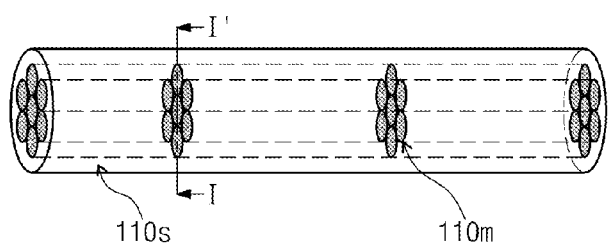
FIG. 6B is a three-dimensional view of a portion of FIG. 6A.
Figure 6C:
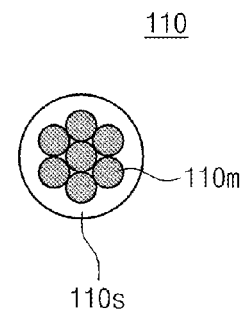
FIG. 6C is a cross-sectional view taken along line I-I' of FIG. 6B.

FIG. 6A is a plan-view image of a target for generating positive ions used in the ion beam treatment apparatus according to the embodiment of the present invention, FIG. 6B is a three-dimensional view of a portion of FIG. 6A, and FIG. 6C is a cross-sectional view taken along line I-I' of FIG. 6B.

Referring to FIGS. 6A to 6C, nanowires 110, which are formed on a thin film for generating positive ions 120 by an electrospinning method, are observed. Each of the nanowires 110 formed by the electrospinning method may have a configuration in which metal nanoparticles are disposed in a polymer shell 110s including a polymer component. That is, each of the nanowires 110 may be composed of a metal nanocore 110m formed of metal nanoparticles and the polymer shell 110s surrounding the metal nanocore 110m.

Figure 7:
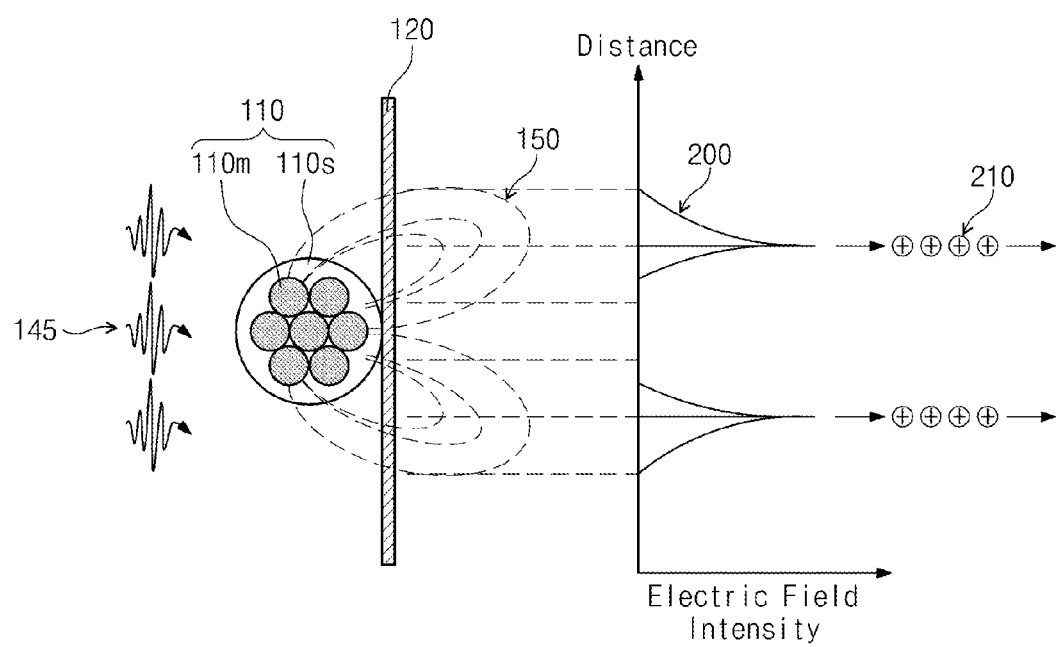
FIGS. 7 and 8 are configuration views illustrating generation of positive ions from targets for generating positive ions used in the ion beam treatment apparatus according to the embodiment of the present invention.
Figure 8:
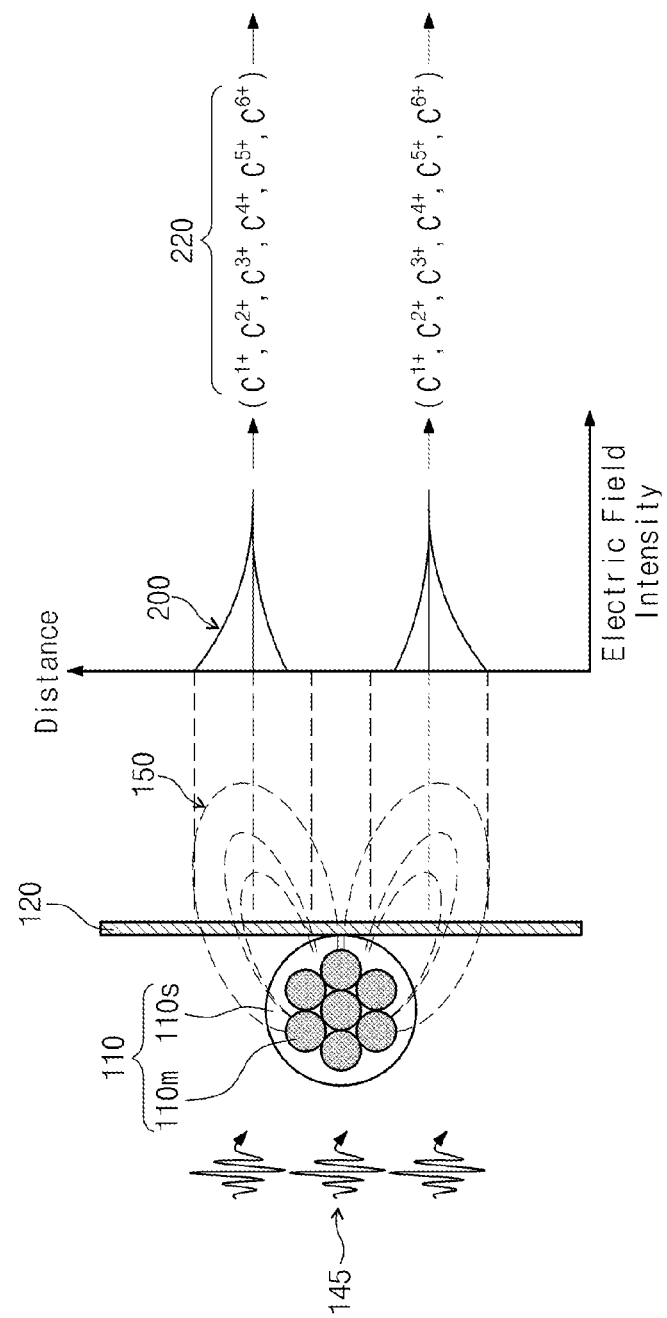

FIGS. 7 and 8 are configuration views illustrating generation of positive ions from targets for generating positive ions used in the ion beam treatment apparatus according to the embodiment of the present invention.

Referring to FIGS. 7 and 8, positive ions, such as protons 210 or carbon ions 220, may be emitted from a thin film for generating positive ions 120 due to a near field 150 generated by a laser beam 145 incident on a nanowire 110.

When the laser beam 145 is incident on a metal nanocore 110m of the nanowire 110, surface waves are generated a near edge of the metal nanocore 110m while free electrons in metal nanoparticles, which are resonated at a frequency of the laser beam 145, collectively move. The generated surface waves generate the near filed 150, a strong electromagnetic field, in a very short distance, i.e., a distance (a few nanometers) near the edge of the metal nanocore 110m. The near field 150 occurs due to the accelerated motion of free electrons in the metal nanoparticles.

An intensity 200 of the near field 150 is the highest at a position in which resonance occurs, i.e., the edge of the metal nanocore 110m of the nanowire 110. The intensity 200 of the near field 150 rapidly decreases as the distance increases from the edge of the metal nanocore 110m of the nanowire 110. A ratio of the intensity 200 of the near field 150 to an intensity of the laser beam 145 incident on the nanowire 110 may range from a few tens to a few tens of thousands.

When the thin film for generating positive ions 120 is exposed under the near field 150 that has an intensity improved by few tens to a few tens of thousands times compared to the intensity of the incident laser beam 145, atoms contained in the thin film for generating positive ions 120 undergo an ionization process to become the protons 210 or the carbon ions 220, and thus, the protons 210 or the carbon ions 220 may be projected to a tumor region (see 340 in FIG. 9) in the body.

Figure 9:
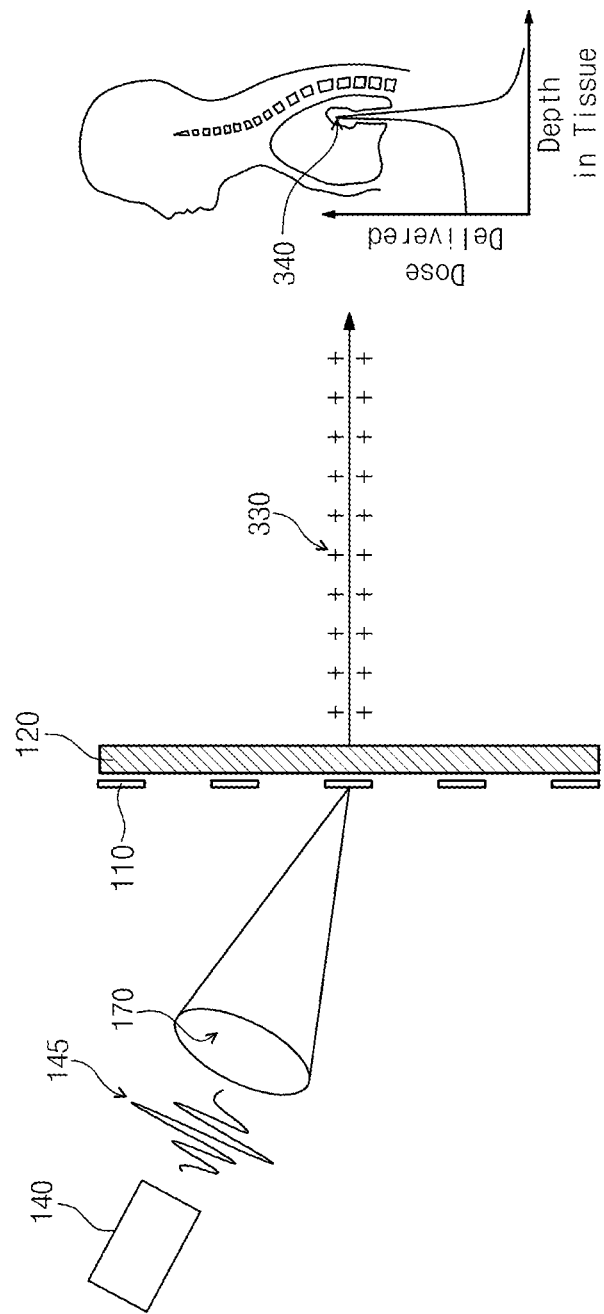
FIG. 9 is a conceptual view illustrating an ion beam treatment apparatus according to an embodiment of the present invention.

FIG. 9 is a conceptual view illustrating an ion beam treatment apparatus according to an embodiment of the present invention.

Referring to FIG. 9, an ion beam treatment apparatus includes a laser 140, an optical member 170, and a target for generating positive ions.

The laser 140 may generate positive ions 330 from the target for generating positive ions to project the positive ions 330 to a tumor region 340 of a patient. The laser 140 may emit a laser beam 145 to the target for generating positive ions. The laser 140 may be disposed on a side opposite to a side of the nanowires 110 facing a thin film for generating positive ions 120 of the target for generating positive ions. The laser beam 145 may be a femtosecond laser beam. A wavelength of the laser beam 145 may be in a range of about 800 nanometers to about 1,000 nanometers. The reason for this is that free electrons in metal nanoparticles constituting a metal nanocore (see 110m in FIG. 7) of each of the nanowires 110 of the target for generating positive ions are resonated by the frequency of the laser beam 145 and thus, may be in accelerated motion.

The target for generating positive ions may generate the positive ions 330 by being irradiated with the laser beam 145 emitted from the laser 140. The target for generating positive ions may include the thin film for generating positive ions 120 and the nanowires 110 with nano-linewidth disposed on one side of the thin film for generating positive ions 120.

The metal nanocore of each of the nanowires 110 may have a linewidth ranging from a few tens to a few hundreds of nanometers. The metal nanoparticles constituting the metal nanocore of each of the nanowires 110 may include a material having relatively high conductivity. That is, the metal nanoparticles may include gold, silver, copper, or aluminum.

The thin film for generating positive ions 120 may generate the positive ions 330 by the incident laser beam 145. The positive ions 330 may be protons, carbon ions, oxygen ions, or nitrogen ions.

In a case where the positive ions 330 are protons, the thin film for generating positive ions 120 may include a material containing hydrogen. The material containing hydrogen may be silicon nitride, silicon oxide, sodium nitride, sodium oxide, or metal. Also, in a case where the positive ions 330 are carbon ions, the thin film for generating positive ions 120 may include graphene.

Alternatively, in a case where the positive ions 330 are protons, carbon ions, oxygen ions, or nitrogen ions, the positive ions 330 may not be generated from the thin film for generating positive ions 120, but may be generated from a polymer shell (see 110s in FIG. 7) of each of the nanowires 110.

The optical member 170 may focus the laser beam 145 to the nanowires 110. The optical member 170 used for focusing the laser beam 145 may be an off-axis parabola mirror.

When the laser beam 145 is incident on the nanowires 110 of the target for generating positive ions, a near field (see 150 in FIG. 7) having an intensity enhanced more than the intensity of the laser beam 145 occurs by surface plasmon resonance of the metal nanocore of each of the nanowires 110. As a result, the positive ions 330 generated from the thin film for generating positive ions 120 of the target for generating positive ions may be protons, carbon ions, oxygen ions, and nitrogen ions, which have a high energy ranging from a few tens to a few hundreds of MeV. That is, since the ions 330 generated from the thin film for generating positive ions 120 of the target for generating positive ions may have energy controlled by the intensity of the near field, the ions 330 may be stopped at a tumor region 340 in the body of a patient, and may collide with the tumor region 340.

When the femtosecond laser beam 145 is accurately focused to the nanowires 110 of the target for generating positive ions, the positive ions 330 are emitted from the thin film for generating positive ions 120 by being accelerated due to the near field formed on the metal nanocore of the nanowires 110 according to the nanoplasmonic phenomenon.

The positive ions 330 may be projected by being set to a position of the tumor region 340 obtained from an image diagnostic apparatus, such as magnetic resonance imaging (MRI), computer tomography (CT), positron emission tomography (PET), and an ultrasonic wave device.

A treatment principle of the ion beam treatment apparatus may be described as follows: the laser beam 145 emitted from the laser 140 is projected to the nanowires 110 of the target for generating positive ions, the positive ions 330 are generated from the thin film for generating positive ions 120 by the near field generated due to the surface plasmon resonance of the metal nanocore of each of the nanowires 110 and projected into the body of a patient, the positive ions 330 projected into the body of the patient are stopped at the tumor region 340 in the body of the patient due to the principle of Bragg Peak as described above and collide therewith, and thus, the positive ions 330 may disturb tumor cells in the tumor region 340 by generating free oxygen radicals.

That is, the positive ions 330 generate free oxygen radicals by colliding with the tumor region 340 to disturb tumor cells of the tumor region 340 and thus, the positive ions 330 may prevent the growth of the tumor cells or may necrotize the tumor cells. That the positive ions 330 disturb the tumor cells in the tumor region 340 may be to disturb a DNA double helix of the tumor cell or to disturb metabolic processes in a tumor cell nucleus.

The generation and projection processes of the positive ions 330 may be described as follows: when the laser beam 145 is incident on the metal nanocore of each of the nanowires 110 of the target for generating positive ions, hydrogen atoms or carbon atoms included in the thin film for generating positive ions 120 by the near filed generated due to the surface plasmon resonance of the metal nanocore are changed into a plasma state in which the hydrogen atoms or the carbon atoms are separated into the positive ions 330 and negative ions (not shown) by the energy of the near field, an electric field occurs due to a capacitor effect between the positive ions 330 and the negative ions as the negative ions are further away from the thin film for generating positive ions 120 than the positive ions 330 during the above process, the positive ions 330 are accelerated toward the negative ions due to the electric field, and thus, the positive ions 330 may be accelerated to have energy sufficient to be projected to the tumor region 340 in the body from the outside of the body of a patient.

The accelerated positive ions 330 collide with the tumor region 340 in the body of the patient and generate free oxygen radicals to disturb tumor cells in the tumor region 340, and thus, the accelerated positive ions 330 may prevent the growth of the tumor cells or may necrotize the tumor cells. As a result, an effect of treating the tumor region 340 in the body of the patient may be exhibited.

Figure 10A:
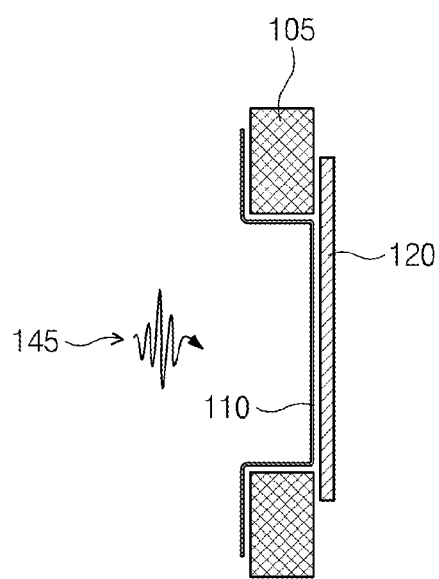
FIGS. 10A and 10B are respectively cross-sectional view and plan view illustrating another target for generating positive ions used in the ion beam treatment apparatus according to the embodiment of the present invention.
Figure 10B:
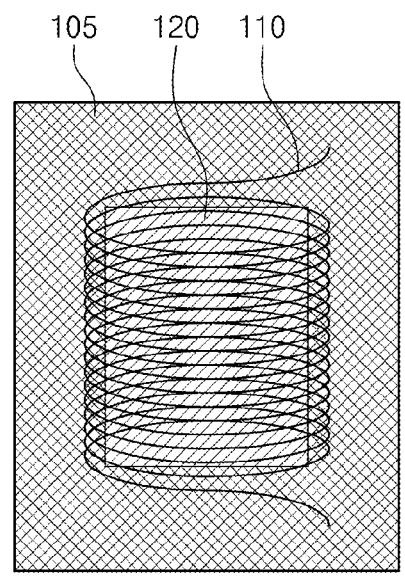

FIGS. 10A and 10B are respectively cross-sectional view and plan view illustrating another target for generating positive ions used in the ion beam treatment apparatus according to the embodiment of the present invention.

Referring to FIGS. 10A and 10B, a target for generating positive ions may include a support 105 with a penetration area exposing a predetermined region, a thin film for generating positive ions 120 attached to one side of the support 105, and a nanowire 110 including a metal nanocore (see 110m in FIG. 7) composed of metal nanoparticles and a polymer shell (see 110s in FIG. 7) surrounding the metal nanocore. Herein, the nanowire 110 may be disposed on the penetration area of the support 105 and a side opposite to a side of the support 105 facing the thin film for generating positive ions 120. That is, the nanowire 110 may be disposed on one side of the thin film for generating positive ions 120 exposed by the penetration area of the support 105. As a result, a laser beam 145 is incident on the nanowire 110 through the penetration area of the support 105 and thus, may generate positive ions (see 330 in FIG. 9) from the thin film for generating positive ions 120.

FIGS. 11A and 11B are respectively cross-sectional view and plan view illustrating another target for generating positive ions used in the ion beam treatment apparatus according to the embodiment of the present invention.

Referring to FIGS. 11A and 11B, a target for generating positive ions may include a support 105 with a penetration area exposing a predetermined region, and a nanowire 110 including a metal nanocore (see 110m in FIG. 7) composed of metal nanoparticles and a polymer shell (see 110s in FIG. 7) surrounding the metal nanocore. Herein, the nanowire 110 may have an extended shape by being disposed on the penetration area of the support 105 and one side of the support 105. That is, the target for generating positive ions may have a structure that does not include a thin film for generating positive ions (see 120 in FIG. 10A or FIG. 10B). As a result, a laser beam 145 is incident on the nanowire 110 through the penetration area of the support 105, and thus, may generate positive ions (see 330 in FIG. 9) from the polymer shell of the nanowire 110.

The reason for generating the positive ions from the polymer shell of the nanowire 110 is that a polymer component of the polymer shell contains atoms, such as carbon, hydrogen, oxygen, and nitrogen. That is, the atoms, such as carbon, hydrogen, oxygen, and nitrogen, contained in the polymer shell are ionized by a near field (see 150 in FIG. 7) formed at the metal nanocore of the nanowire 110, and the ionized positive ions may be accelerated.

FIG. 12 is a configuration view illustrating generation of positive ions from the target for generating positive ions of FIGS. 11A and 11B used in the ion beam treatment apparatus according to the embodiment of the present invention.

Referring to FIG. 12, as described in FIGS. 11A and 11B, when a laser beam 145 is incident on a metal nanocore 110m of a nanowire 110, atoms, such as carbon, hydrogen, oxygen, and nitrogen, contained in a polymer shell 110s are ionized by a near field 150 formed at the metal nanocore 110m, and the ionized positive ions 220 may be accelerated.

Herein, the positive ions 220 emitted by being accelerated from the polymer shell 110s of the nanowire 110 may be various, such as protons, carbon ions, oxygen ions, and nitrogen ions. However, an ion beam treatment apparatus generally uses a single type of positive ions. The reason for this is that acceleration energy of positive ions is determined by calculating a depth of a tumor region (see 340 in FIG. 9), wherein the depths reached by multiple types of positive ions may be different from one another when there are many types of the positive ions, and thus, it may be difficult to effectively treat the tumor region. However, with respect to a treatment simultaneously requiring multiple types of positive ions, it may be relatively advantageous in using the multiple types of positive ions. For the simplicity of the description, multiple types of the positive ions 220 are typically illustrated as various carbon ions.

According to embodiments of the present invention, since a target for generating positive ions has a metal nanocore, an intensity of a laser beam incident on the target for generating positive ions may be enhanced. As a result, a target for generating positive ions, which may generate high-energy positive ions while not increasing a laser output, may be provided.

Also, since nanowires having a metal nanocore are formed on a thin film for generating positive ions prepared according to the embodiments of the present invention, the intensity of the laser beam incident on the target for generating positive ions may be enhanced. As a result, a method of fabricating a target for generating positive ions, which may generate high-energy positive ions while not increasing a laser output, may be provided.

Furthermore, since an ion beam treatment apparatus, according to the embodiments of the present invention, uses a target for generating positive ions having a metal nanocore, high-energy positive ions may be projected to a tumor region of a patient. As a result, an ion beam treatment apparatus capable of treating tumors in a patient at a low cost may be provided.

While preferred embodiments of the present invention has been particularly shown and described with reference to the accompanying drawings, it will be understood by those of ordinary skill in the art that various changes in form and details may be made therein without departing from the spirit and scope of the present invention as defined by the following claims. Therefore, the preferred embodiments should be considered in descriptive sense only and not for purposes of limitation.

What is claimed is:

1. A target for generating positive ions comprising:
a thin film for generating positive ions; and
nanowires provided on at least one side of the thin film for generating positive ions,
wherein each of the nanowires comprise a metal nanocore and a polymer shell surrounding the metal nanocore, and
the thin film for generating positive ions generates positive ions by a laser beam incident on the nanowires.

2. The target for generating positive ions of claim 1, wherein the metal nanocore is composed of metal nanoparticles.

3. The target for generating positive ions of claim 2, wherein the metal nanoparticles comprise gold, silver, copper, or aluminum.

4. The target for generating positive ions of claim 2, wherein the nanowires are formed by electrospinning a polymer solution including the metal nanoparticles.

5. The target for generating positive ions of claim 1, wherein the metal nanocore has a linewidth ranging from a few tens to a few hundreds of nanometers.

6. The target for generating positive ions of claim 1, wherein the positive ions are protons, carbon ions, oxygen ions, or nitrogen ions.

7. The target for generating positive ions of claim 6, wherein the positive ions are protons and the thin film for generating positive ions comprises a material containing hydrogen or sodium.

8. The target for generating positive ions of claim 7, wherein the material containing hydrogen or sodium is silicon nitride, silicon oxide, sodium nitride, sodium oxide, or metal.

9. The target for generating positive ions of claim 6, wherein the positive ions are carbon ions and the thin film for generating positive ions comprises graphene.

10. The target for generating positive ions of claim 6, wherein the positive ions are protons, carbon ions, oxygen ions, or nitrogen ions, and the positive ions are generated from the polymer shell.

11. The target for generating positive ions of claim 1, further comprising a support which is attached to an edge of the thin film for generating positive ions and supports the thin film for generating positive ions.

12. An ion beam treatment apparatus comprising:
the target for generating positive ions of claim 1; and a laser for emitting a laser beam incident on nanowires to project positive ions to a tumor region of a patient by generating the positive ions from a thin film for generating positive ions, wherein the laser beam incident on the nanowires forms surface plasmon resonance, a near field having an intensity enhanced more than an intensity of the laser beam is formed by the surface plasmon resonance, and the positive ions are emitted from the thin film for generating positive ions by the near field.

13. The ion beam treatment apparatus of claim 12, wherein the laser is disposed on a side opposite to a side of the nanowires facing the thin film for generating positive ions.

14. The method of claim 12, wherein the laser beam is a femtosecond laser beam.

15. The method of claim 12, wherein a ratio of an intensity of the near field to the intensity of the laser beam ranges from a few tens to a few tens of thousands.

16. A method of fabricating a target for generating positive ions, the method comprising forming nanowires respectively including a metal nanocore and a polymer shell surrounding the metal nanocore on one side of a thin film for generating positive ions having both opposing sides by using an electrospinning method, wherein the metal nanocore forms surface plasmon resonance by an incident laser beam, a near field having an intensity enhanced more than an intensity of the laser beam is formed by the surface plasmon resonance, and positive ions are emitted from the thin film for generating positive ions by the near field.

17. The method of claim 16, wherein the forming of the nanowires by using an electrospinning method comprises:

preparing a polymer solution containing metal nanoparticles; and applying a voltage between the polymer solution and the thin film for generating positive ions.

18. The method of claim 17, wherein the metal nanoparticles comprise gold, silver, copper, or aluminum.

19. The method of claim 16, wherein the nanowires are formed to allow the metal nanocore to have a linewidth ranging from a few tens to a few hundreds of nanometers.

20. The method of claim 16, wherein the thin film for generating positive ions comprises a material containing hydrogen or sodium, or graphene.

\* \* \* \* \*